(12) United States Patent
Spies et al.

(10) Patent No.: US 8,050,477 B2
(45) Date of Patent: Nov. 1, 2011

(54) RADIATION THERAPY FLANNING PROCEDURE

(75) Inventors: Lothar Spies, Hamburg (DE); Helga Hummel, Aachen (DE); Carolina Ribbing, Aachen (DE); Ralf Hoffmann, Brüggen (DE); Peter Klaus Bachmann, Würselen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 729 days.

(21) Appl. No.: 12/162,671

(22) PCT Filed: Jan. 22, 2007

(86) PCT No.: PCT/IB2007/050204
§ 371 (c)(1),
(2), (4) Date: Jul. 30, 2008

(87) PCT Pub. No.: WO2007/008492
PCT Pub. Date: Aug. 9, 2007

(65) Prior Publication Data
US 2009/0028408 A1 Jan. 29, 2009

(30) Foreign Application Priority Data
Feb. 1, 2006 (EP) .................................. 06101133

(51) Int. Cl.
*A61N 5/10* (2006.01)
(52) U.S. Cl. ........................................... 382/131; 378/65
(58) Field of Classification Search .................. 378/62, 378/64, 65; 382/128, 130, 132, 284, 294
See application file for complete search history.

(56) References Cited

U.S. PATENT DOCUMENTS

| | | | |
|---|---|---|---|
| 6,159,702 A * | 12/2000 | Traish | 435/7.23 |
| 6,363,772 B1 | 4/2002 | Berry | |
| 6,379,647 B2 | 4/2002 | Lewis | |
| 6,489,113 B1 * | 12/2002 | Traish | 435/6 |
| 7,257,243 B2 * | 8/2007 | Schmidt et al. | 382/128 |

FOREIGN PATENT DOCUMENTS

| | | |
|---|---|---|
| EP | 1475127 A1 | 11/2004 |
| WO | WO0107414 A1 | 2/2001 |

OTHER PUBLICATIONS

Eschmann et al: "Prognostic Impact of Hypoxia Imaging With 18F-Misonidazole Pet in Non-Small Cell Lung Cnacer and Head and Neck Cancer Before Radiotherapy"; Journal of Nuclear Medicine 2005, vol. 46 (2), pp. 253-260.
Yang et al: "Towards Biologically Conformal Radiation Therapy (BCRT): Selective IMRT Dose Escalation Under the Guidance of Spatial Biology Distribution"; Medical Physics, AIP, vol. 32, No. 6, May 11, 2005, pp. 1473-1484.
Casciari et al: A Modeling Approach for Quantifying Tumor Hypdxia With UF-18 Fluoromisonidazole Pet Time-Activity Data; Medical Physics, AIP, vol. 22, No. 7, Jul. 1, 1995, pp. 1127-1139.
Rasey et al: "Quantifying Regional Hypoxia in Human Tumors With Positron Emission Tomography of [18} Flyoromisonidazole: A Pretherapy Study of 37 Patients"; International Journal of Radiation Oncology Biology Physics, vol. 36, No. 2, Sep. 1, 1996, pp. 417-428.
Apisarnthanarax et al: "Current Imaging Paradigms in Radiation Oncology"; Radiation Research, vol. 163, No. 1, 2005, pp. 1-25.
Rizzo et al: "Integration of Cupet Images for the Optimization of Radiotherapy Planning" Proceedings of the 23rd Annual International Conference of the IEEE Engineering in Medicine and Biology Society, Instanbul, Turkey, Oct. 25-28, 2001, IEEE, vol. 1 of 4, Conference 23, pp. 2756-2758.
Xing et al: "Inverse Planning for Functional Image-Guided Intensity-Modulated Radiation Therapy"; Physics in Medicine and Biology, vol. 47, No. 20, Oct. 21, 2002, pp. 3567-3578.
Srinivas et al:"Proteomics in Early Detection of Cancer"; Clinical Chemistry, vol. 47, pp. 1901-1911, 2001.
Piert et al: "Hypoxia-Specific Tumor Imaging With 18F-Fluoroazomycin Arabinoside"; Journal of Nuclear Medicine, vol. 46, No. 1, pp. 106-113, 2005.
Webb, S.: "Intensity-Modulated Radiation Therapy"; Institue of Physics Publishing Ltd, 2001, Chapter 3, pp. 75-97.

* cited by examiner

*Primary Examiner* — Irakli Kiknadze

(57) ABSTRACT

An improved radiation therapy planning procedure is suggested. The procedure comprises the steps of specifying and determining the absolute grade of cell degeneracy by in-vitro tests, whereby marker(s) indicative for specific cell degeneracy are detected and quantified, establishing a biology-based segmentation of areas with similar grade of relative cell degeneracy and applying the absolute grade of cell degeneracy to the biology-based segmentation data, thereby establishing an improved radiation therapy planning procedure. Moreover, the present invention suggests a system for an improved radiation therapy planning procedure and its use in procedures of diagnosis and/or therapy management of cancer.

24 Claims, No Drawings

RADIATION THERAPY PLANNING PROCEDURE

The present invention pertain an improved procedure for planning radiation therapy as well as systems to realize a protocol for establishing said therapy plan and use thereof especially in cancer research and management of radiotherapy.

Early medical diagnosis and therapy of cancer tumours is of tremendous importance in medicine. For example, lung cancer is the second leading cancer incidence in men and women contributing to 14% and 12%, respectively, of all new cancer cases in the western world. It is the leading cause of cancer deaths in men and women with the lowest 5-year survival rate of all major cancer diseases (breast, prostate, colorectal). An estimated 172,000 cases of lung cancer were expected in 2004 alone in the US.

In the last two decades, intense investigations were made in the field of medical imaging. Advanced techniques thereof are CT (computed tomography), MRI (magnetic resonance imaging), PET (positron emission tomography), SPECT (single photon emission computed tomography) or US (ultrasound).

Computed tomography (CT) and magnetic resonance imaging (MRI) are well-known technologies for visualizing human anatomy, especially with the focus on tissue abnormality.

Positron emission tomography (PET) is an imaging modality that allows studying physiological, biochemical and pharmacological functions at a molecular level. The PET methodology permits the measurement of physiological parameters such as blood flow or receptor concentrations. In addition, the method allows obtaining quantitative information on the pharmacokinetics and pharmacodynamics of biomolecule(s) in living animals.

$^{18}$F-FDG (fluorinated deoxy-glucose) has been recognized as the "gold standard" PET agent for imaging cancerous lesions and its use in oncology has been widely documented.

PET studies with $^{18}$F-FDG in head and neck cancer, malignant lymphoma, breast cancer, lung cancer, liver cancer and colon cancer have been reported.

This widespread use of $^{18}$F-FDG is based on the fact that glucose metabolism is higher in tumour than in normal tissues. In the cell, $^{18}$F-FDG is phosphorylated by hexokinase to $^{18}$F-FDG-6-phosphate. In contrast to glucose, $^{18}$F-FDG-6-phosphate is not metabolized further and is essentially trapped in cells. The extent of accumulation of $^{18}$F-FDG in the cell reflects the degree of glucose uptake and phosphorylation and its accumulation in cancerous cells can be assessed with quantitative and semi-quantitative methods resulting in important anatomical and functional information about malignancy.

Although $^{18}$F-FDG is the preferred PET pharmaceutical in oncology, it has some well-known shortcomings.

These include its inability to visualize brain tumours due to high normal cell uptake and to differentiate between tumour cells and chronic inflammation. In order to overcome the weaknesses of $^{18}$F-FDG in visualizing cancerous cells, efforts were made in the past years to develop new PET agents that lack these shortcomings.

As a result, a large number of oncological imaging agents have emerged. Some of these agents are currently under clinical investigation or in clinical use and serve as additional tools for studying other aspects of tumour biochemistry, excluding glucose metabolism.

One disadvantage of these new imaging agents is that the corresponding imaging procedures are very time consuming and thus not always suitable for routine diagnosis. Moreover, these agents and the corresponding imaging procedures are very expensive and thus difficult to apply on a larger patient cohort. Therefore, the decision to use a highly specific target needs to be well considered, both under clinical and economical aspects.

Another problem is that it is often a process of trial and error to decide if a patient is a good candidate for a highly specific imaging procedure or not.

In these cases, costs for diagnosis are increased tremendously; e.g., estimated additional costs for a highly specific imaging agent are US \$2.000 per patient. However, the most important disadvantage is, that time is wasted, which might have fatal consequences for the patient.

Yet another problem of tumour diagnosis and therapy is, that in many cases there exist a non-uniform, heterogeneous distribution of tumour cells with respect to extent and level of degeneracy. This means, areas with more or less aggressive malignancy phenotypes co-exist within the defined tumour region. Highly aggressive tumour cells are often less sensitive (or more resistant) to radiation and/ or chemotherapeutics resulting in increased failure of radiotherapy. Sometimes, this aggressiveness is correlated to lack or absence of oxygen in the cells (hypoxia).

Recently, radiation dose distribution (non-uniform dose pattern) based on spatial distribution according to anatomical and/or functional imaging information was described through an equation disclosed in Y. Yang and L. Xing (Med. Phys., 32 (6), 2005). However, the described doses comprise relative factors ($D_{rel}$) based on wisdom and experience and still leave a high potential of uncertainty concerning the real situation and absolute grade of individual malignancy.

This uncertainty in determination of dose often results in increased occurrence of tumour cell proliferation and metastasis as well as malignant recidivism. In order to overcome this, absolute radiation dose is often increased, however resulting in higher radio-mortality of patients.

The provision of a procedure for a faster, more accurate, more individual, more cost-efficient, early diagnosis and prognosis, resulting in efficiently increased patient benefit and success of therapy, because of an more individual establishment, adaptation and optimization of treatment protocol, such as radiation- and/or chemo-therapy, which improve tumour control and reduce ratio of metastasis, recidivism and patient radio- and/or chemo-mortality is highly desirable.

The invention therefore suggests an improved radiation therapy planning procedure comprising the steps of
  a) specifying and determining the absolute grade of cell degeneracy by in-vitro tests, whereby marker(s) indicative for specific cell degeneracy are detected and quantified,
  b) establishing a biology-based segmentation of areas ($k_\alpha$, $k_\beta$, $k_\gamma$) with similar grade of relative cell degeneracy in accordance to information acquired during functional imaging and/or anatomical imaging,
  c) applying the absolute grade of cell degeneracy acquired in step a) to the biology-based segmentation data, thereby establishing an improved radiation therapy planning procedure.

In one embodiment of the present invention, anatomical data are acquired prior to specification and determination of absolute grade of cell degeneracy in in-vitro tests. In another embodiment of the present invention, specification of cell degeneracy via in-vitro tests is executed prior to functional imaging, in order to select the most suitable imaging agent(s) available with respect to the patient-specific type of cell degeneracy and with respect to functional imaging, respectively. In a further embodiment of the present invention functional imaging is executed prior, during or subsequent to in-vitro tests.

In one advantageous embodiment of the present invention, an improved radiation therapy planning procedure is suggested comprising the steps of
   a) acquiring anatomical imaging information,
   b) specifying and determining the absolute grade of cell degeneracy by in-vitro tests, whereby marker(s) indicative for specific cell degeneracy are detected and quantified,
   c) acquiring functional imaging information,
   d) establishing a biology-based segmentation of areas ($k_{60}$, $k_\beta$, $k_\gamma$) with similar grade of relative cell degeneracy in accordance to information acquired in step a) and c),
   e) applying the absolute grade of cell degeneracy acquired in step b) to the biology-based segmentation data, thereby establishing an improved radiation therapy planning procedure.

In another advantageous embodiment of the invention, the anatomical and/or functional imaging process is selected from the group of CT (computed tomography), SPECT (single photon emission computed tomography), PET (positron emission tomography), MRI (magnetic resonance imaging), US (ultrasound), OI (optical imaging), TI (thermal imaging) or X-ray or any combination thereof.

Preferably, the anatomical imaging process is CT or MRI.

The information acquired with anatomical imaging gives a first set of intermediate patient data concerning localisation and extent of degenerated cells.

In another advantageous embodiment of the invention multimodality processes like CT/PET, MRI/PET or CT/MRI/PET are used to acquire more exact imaging information, as for example the more exact determination of tumour boarders within the degenerate tissue or the status of proliferation/metastasis. A more favourable variant of the invention is a multimodality imaging process via combined CT/$^{18}$F-FDG-PET procedure. In one embodiment of the present invention, data acquired with anatomical and functional imaging are co-registered.

The expression "degeneracy" or "degenerate" in the sense of the present invention might be used synonymous with diseased, neoplastic, cancerous, malignant or benignant tumours and means abnormal or the opposite of normal or healthy, respectively.

The expression "cells" in the sense of the present invention means every material with biological activity and natural or synthetic origin and might be used synonymous with biomaterial. It comprises for example body fluids like blood, serum, urine, spinal fluid, lymph or salvia, tissue, tissue cultures, organelles or organs, but is not limited to these.

In the invention, the absolute grade of cell degeneracy is specified and determined by in-vitro tests, whereby marker(s) indicative for specific cell degeneracy are detected and quantified.

This step can be carried out prior, during or subsequent to anatomical imaging in the sense of the present invention.

In the present invention, the determined absolute grade of cell degeneracy provides the important advantage that the relative grade of cell degeneracy (acquired in functional imaging, dynamic functional imaging, pharmacokinetic analysis and corresponding correlations to biologically relevant parameters, clustering and/or correction or any combination thereof) is calibrated or normalized by adapting the absolute quantity of degeneracy as a weighting or correction factor to the segments (areas, tumour volumes) with relative degeneracy.

"Markers" or "biomarkers" might be used synonymous and in the sense of the present invention means every naturally occurring or produced, or synthetically generated material with a specific biological activity, suitable for illustrating a special situation of degenerate cells in-vivo or in-vitro. These are for example any kind of nucleic acids (e.g. genes, gene fragments or gene mutations), proteins, peptides, antibodies or antibody fragments and any material, which can be analyzed by in-vitro tests.

Biomarkers are important tools for disease detection and monitoring. They serve as hallmarks for the physiological status of a cell at a given time and may change during the disease process. For example, gene mutations, alterations in gene transcription and translation, and alterations in their protein products, metabolically transformed proteins or peptides and any combination of such biomarkers in the format of multi-marker panels can potentially serve as specific biomarkers for a disease.

"In-vitro tests" in the sense of the present invention comprise genetic and/or proteomic techniques or test to identify or quantify metabolites correlated with cell degeneracy. This means, tests that evaluate nucleic acids of any kind or that rely on amino acids and their variants or that rely on metabolites correlated with cancer.

In-vitro tests are understood in the sense of the present invention as a multitude of processes employed in identifying, quantifying or deciphering the form, function and interactions of genes or proteins or metabolites, respectively.

Many diseases are caused by malfunction or absence of proteins. The application of said in-vitro technologies to current areas of clinical investigation, including the use of such technologies in diagnostics allows to simultaneously and comprehensively examine changes in a very large numbers of genes or proteins in the context of disease development or progression or other changes in physiological conditions. This provides an excellent tool to solve important clinical problems, including early diagnosis.

Therefore, one advantage of the present invention using in-vitro test of biomarkers corresponding to malfunction or absence of proteins, is the early and precise diagnosis of diseases, staging and follow-up after treatment to early detect reoccurrences (recidivism).

In an alternative advantageous embodiment of the invention genomic and/or proteomic techniques and/or techniques to identify cancer characteristic metabolites are high-through-put screening and analysis procedures, respectively, realized for example on biochips or with the help of biosensor devices.

Advances in genomic technologies have made it possible to rapidly screen for global and specific changes in gene expression that occur only in cancer cells, but not in healthy cells.

Not all changes in gene expression might be reflected at the level of protein or metabolic function. Therefore, protein-based assays or proteomic techniques are important complementing in-vitro tests.

In an alternative embodiment of the invention, said in-vitro tests comprising for example, gene expression profiling, differential display, gel electrophoresis, SAGE, PCR, reverse transcriptase-PCR, quantitative real-time-PCR, protein assays, ELISA (Enzyme Linked Immunosorbent Assay) or any kind of mass spectrometry-(MS)-based techniques or any combination thereof.

Said techniques might be used with or without additional steps of cleaning, fractionation or enrichment of probe material.

In a more advantageous embodiment of the invention, the in-vitro test is protein/peptide mass spectrometry (MS) by MALDI (Matrix Assisted Laser Desorption Ionization) or SELDI (Surface Enhanced Laser Desorption Ionization), preferably by MALDI-ToF-MS or SELDI-ToF-MS.

MALDI/SELDI-MS has the advantage of a parallel, analytic approach of disease-indicating biomarkers.

One great advantage of the present invention so far is that it allows a rapid acquisition of patient data and consequently a significant reduction of time for early diagnosis of cancer. This increases the chance of patient's rescue enormously, because subsequent steps in planning the therapy procedure, for example selection of highly specific contrast agents for further imaging procedures or establishment of radiation or chemotherapeutical dose, can be realized much faster and more accurate and specific, as will be discussed below.

Another advantageous variation of the invention is an improved radiation therapy planning procedure, wherein the CAP43 protein (or its corresponding synonyms) indicative for hypoxia is determined by an in-vitro test.

Yet another advantageous variation of the invention is an improved radiation therapy planning procedure, wherein CAP43 protein, modifications thereof, metabolic products generated during modification or any combination of proteins and/or metabolic products indicative for hypoxia is determined by an in-vitro test.

The following expressions might be used synonymous in the sense of the present invention:

CAP43, CMT4D, DRG1, HMSNL, Ndr1, NDRG1, NMSL, N-myc downstream regulated gene 1 protein, PROXY1, RTP, Tdd5 or TDD5.

There exist at least two variants for NDRG 1, namely NDRG 1_Human 42835 Da and NDRG1_Mouse 43009 Da.

To date, the detection of biomarkers using SELDI-MS is possible with a sensitivity in a range of about >30 pg/ml of biological probe of interest, e.g. marker in blood serum. These enumerations and ranges are used to illustrate the present invention, but are not limiting.

Another advantageous embodiment of the invention comprises the step of selecting at least one targeted imaging agent specific for the detected indication of cell degeneracy.

It is one great advantage of the present invention that data acquired in in-vitro tests of the invention allow this selection.

This has the important effect that targeted agent and patients medical indication are matched, resulting in more specific and accurate functional imaging.

One very important effect is an enormous increase in cost-efficiency of the functional imaging procedure and consequently of the whole therapy planning procedure of the present invention. This is, because highly specific targeted contrast agents, which are very expensive, are used only if the corresponding indication has been confirmed.

Several oncological imaging agents are known, for example $^{18}$F-fluoromisonidazole ($^{18}$F-FMISO) for measuring tumour hypoxia, $^{18}$F-3'-fluoro-3'-deoxy-thymidine ($^{18}$F-FLT) for measuring cell proliferation, $^{11}$C-choline for measuring choline kinase activity and $^{18}$F-fluoroethyl tyrosine ($^{18}$F-FET) for measuring amino acid transport rate. IAZA (iodinated azomycine arabinocide) is another imaging agent, especially for SPECT. Also, $^{18}$F-FAZA (fluorinated azomycine arabinocide) is known for PET imaging.

In an advantageous embodiment of the invention, the functional imaging process is PET or SPECT, preferably $^{18}$F-FMISO-PET.

$^{18}$F-FMISO is reduced in hypoxic cells (but not in aerobic cells) resulting in toxic bioreductive products that target hypoxic cells.

"Targeted imaging agent" in the sense of the present invention means targeted imaging contrast agents or a combination of targeted imaging contrast agents and targeted therapeutic agents. Some targeted agents with combined features of increasing imaging contrast and providing therapeutic effect are already art-known, but the invention is not limited to this end.

"Targeted" in the sense of the present invention means that the imaging agent comprises specific features for trapping to or accumulating in a specific target. "Targeted" might also mean that the imaging agent comprises features that specifically direct the imaging agent to its target, e.g. mediated via key/hole-, substrate/enzyme- or antigen/antibody-interaction. Further interaction-couples and all combinations thereof are included in the present invention and intend to illustrate the present invention, but are not limiting.

In the invention, functional imaging is used to acquire information concerning spatial distribution of areas (volumes, regions, sub-regions, which are used synonymous in the sense of the present invention) with different values of activity. In one advantageous variant of the present invention, the obtained data are further processed by pharmacokinetic analysis, clustering techniques and/or correction steps, respectively.

In one embodiment of the present therapy planning procedure, a biology-based segmentation of areas (volumes) with similar grade of relative cell degeneracy (e.g. $k_\alpha$, $k_\beta$, $k_\gamma$) is established in accordance to information acquired in functional and/or anatomical imaging of the present invention.

In order to better characterize target regions and risk cells/organs with respect to radiation sensitivity, the improved radiation therapy planning procedure of the present invention provides a biology-based segmentation step (modelling and/or clustering optionally followed by correction step(s)) that is performed on functional imaging data and/or on already co-registered anatomical and functional imaging data, resulting in areas with similar grade of cell degeneracy.

"Biology-based segmentation" in the sense of the present invention comprises e.g. the following steps:

In a first step, anatomical and functional imaging information is acquired and optionally co-registered. Prior, during or subsequent to this, pharmacokinetic analysis/modelling of imaging information (dynamic series of functional images) is executed yielding a parametric map of biologically relevant (correlated) parameters. Because not only functional imaging data but also anatomical data include information concerning biologically relevant parameters, e.g. tumour contour and volume, acquired anatomical data or a combination (co-registration) of functional and anatomical imaging data can be further processed via pharmacokinetic analysis resulting in a parametric map in the sense of the present invention. Data of said parametric map are further processed by clustering techniques optionally followed by step(s) of data correction to yield a biology-based segmentation of areas (volumes) with similar grade of cell degeneracy, corresponding to similar grade of radio sensitivity, because of e.g. similar degeneracy of cells, tissues or tumours.

These areas with similar grade of cell degeneracy are for example labelled $k_\alpha$, $k_\beta$, $k_\gamma$, representing weak, medium and strong cell degeneracy (e.g. malignancy of tumours), respectively. In the sense of the present invention, all sub-ranges from no cell degeneracy via weak, medium or high to strong cell degeneracy are included.

In another advantageous embodiment of the invention, the improved radiation therapy planning procedure comprises step(s) of modelling, clustering and/or correcting acquired imaging information.

"Correction" in the sense of the present invention can be the use of morphological filter techniques/ operations.

One embodiment of the present invention is the provision of procedures of/ means for modelling, clustering and/or correcting which can be realized by software-implemented algorithms and/or computer programs and/or empiric correlations which manage the acquisition, storage, transfer, analysis, grouping, combination, modelling, clustering, correction, optimization, application and/or visualization of the acquired intermediate patient data to and from patient databases.

One possible variation of the present invention displays an automated (computer- and/or robot-controlled) procedure for improved therapy planning.

Functional imaging information can be provided as a single image or a set of images from the same modality or different modalities. For the same modality, images can be acquired in a dynamic mode, meaning that a series of images is taken over a longer period of time.

Additionally, various targeted imaging agents in the sense of the present invention may be combined.

In one embodiment of the present invention, a pharmacokinetic analysis/modelling of imaging information is performed, thereby extracting the parameters of interest with respect to the relevant biological parameters from a single image or multiple images, resulting in a parametric map of better specificity (e.g. of tumour aggressiveness) and sensitivity (e.g. for radiation).

For example, pharmacokinetic analysis of time series of functional images enables an accurate quantification of rate constants of physiological processes, such as uptake, trapping or washout of a contrast agent in a given tissue. Compartment modelling is then utilized to extract those rate constants by deploying non-linear regression.

In other embodiments, functional data, such as activity maps, are converted into standard uptake values. Use of standard uptake values provides a model that is less dependent on patient weight and other disease independent parameters. However, use of standard uptake values depends on the imaging agent that is used as some imaging agents require more sophisticated modelling techniques.

In another embodiment of the present invention, the modelling step of biology-based segmentation combines the parametric maps with the anatomical data (or e.g. co-registered functional and anatomical imaging data) in order to cluster the imaged region(s) into a functionality-dependent number of sub-regions (areas, volumes e.g. $k_\alpha$, $k_\beta$, $k_\gamma$) with similar grade of cell degeneracy.

For example, the contour of the degenerated cells (tumour) is outlined using the anatomical imaging data and by clustering these data with data acquired in the parametric map. The investigated region(s) is/are segmented into sub-regions (areas, volumes) with similar grade of cell degeneracy. Each sub-region (area, volume) has a similar radiation sensitivity, and thus requires, or can tolerate, a similar radiation dose during radiation treatment.

In one embodiment of the present invention, a k-mean classifier clustering technique can be performed on the parametric map to cluster the pixels of degenerated cells into areas of similar grade of degeneracy (e.g., labeled $k_\alpha$, $k_\beta$, $k_\gamma$ representing weak, medium and strong degeneracy of cells, respectively). Alternative clustering techniques such as for example c-mean classifier, fuzzy-c-mean classifier or unsupervised Bayesian classifier can be applied which are well known to skilled artisans.

The total number of sub-regions (areas, volumes) depends on the noise content and the parameter range of the parametric map. This is because two classes can generally be discriminated in a noisy environment if the difference of the class-representative intensities ΔS is at minimum five times greater than the noise σs. This is based on the model of image detection which states similar criteria for a reliable detection of a uniform object in a noisy background, namely that the ratio of signal difference and noise shall be greater than five, or:

$$\frac{\Delta S}{\sigma_S} \geq 5 \tag{1}$$

Consequently, the number of areas can be determined in accordance with:

$$\# \text{areas} = \frac{k_{MAX} - k_{MIN}}{K \cdot \langle \sigma_k \rangle} \tag{2}$$

in which, $k_{MAX}$ and $k_{MIN}$ are the maximum and minimum parameter value, respectively, of the target volume; $\langle \sigma_k \rangle$ is the standard deviation representative of the noise in the parametric map; and K is a constant with a value of five or greater according to (1). It should be appreciated that K can be experimentally determined in order to optimize the system.

Thus, the biology-based segmentation represents the relative radiation sensitivity distribution across target volume and cells at risk in the sense of the present invention.

In another variant of the present invention, the improved radiation therapy planning procedure, especially the biology-based segmentation, may optionally include a correction step.

Correction of the clusters incorporates prior knowledge through advanced image processing tools, such as morphological filter techniques, morphological operations and expert knowledge to correct falsely clustered domains. Correction can be automatic (computer- and/or robot-controlled) or semi-automatic, to reduce cluster sizes by a predetermined percentage, or can be done manually by the physician via a graphical user interface.

In the present invention, the absolute grade of cell degeneracy according to information acquired in in-vitro tests is applied to the data of biology-based segmentation, thereby establishing an improved radiation therapy planning procedure.

Here, the data of in-vitro test pattern profiling of markers are combined with bioinformatics and imaging data. Thereby a device such as the PINNACLE™ radiation treatment planning device manufactured by Philips Medical Systems can be used.

Another advantageous embodiment of the invention, the integration of absolute and relative grade of cell degeneracy is managed according to the equation:

$$D(k; G_{cell\ degeneracy}) = D_0 + \frac{k - k_\alpha}{k_\gamma - k_\alpha} \cdot \Delta D(G_{cell\ degeneracy})$$

where is hypothesized: $\Delta D \propto G_{cell\ deg\ eneracy}$
and wherein
$G_{cell\ deg\ eneracy}$=absolute grade of cell degeneracy,
D=absolute dose of radiation prescribed according to determined biological parameters
$D_0$=dose of radiation according to standard protocol,
ΔD =dose of radiation correlated to absolute cell degeneracy, k, $k_\alpha$, $k_\gamma$=area with similar grade of relative cell degeneracy.

A preferred embodiment of the present invention is given through an improved radiation therapy planning procedure comprising the steps of
- a) acquiring anatomical imaging information in CT,
- b) specifying and determining the absolute grade of cell degeneracy by in-vitro tests, whereby CAP43 protein, modification thereof, metabolic products generated during modification or any combination of proteins and/or metabolic products indicative for hypoxia is detected and quantified,
- c) selecting $^{18}$F-FMISO as targeted imaging agent,
- d) acquiring functional imaging information in $^{18}$F-FMISO-PET,
- e) establishing a biology-based segmentation of areas ($k_\alpha$, $k_\beta$, $k_\gamma$) with similar grade of relative hypoxia in accordance to information acquired in step a) and d),
- f) applying the absolute grade of hypoxia according to information acquired in step b) to the biology-based segmentation data, thereby establishing an improved radiation therapy planning procedure.

In another advantageous embodiment of the invention, step(s) of modelling, clustering and/or correcting of the acquired information are carried out prior, during and/or subsequent to steps of in-vitro tests, functional imaging, segmentation and application of absolute and relative values of cell degeneracy (steps b), c), d), e) and f)), respectively.

Said modelling, clustering and/or correction can be realized by provision of software-implemented algorithms and/or computer programs and/or empiric correlations, which manage the acquisition, storage, transfer, analysis, grouping, combination, modelling, clustering, correction, optimization, application and/or visualization of the acquired intermediate patient data to and from patient databases.

One possible variation of the present invention displays an automated (computer- and/or robot-controlled) procedure for improved therapy planning.

The present invention further suggests a system for improved planning of radiation therapy procedure comprising
- a) means for specifying and determining the absolute grade of cell degeneracy by in-vitro tests, whereby marker(s) indicative for specific cell degeneracy are detected and quantified,
- b) means for establishing a biology-based segmentation of areas ($k_\alpha$, $k_\beta$, $k_\gamma$) with similar grade of relative cell degeneracy in accordance to information acquired in functional and/or anatomical imaging,
- c) means for applying the absolute grade of cell degeneracy acquired in in-vitro tests to the biology-based segmentation data, thereby establishing an improved radiation therapy planning procedure.

Another advantageous variant of the present invention suggests a system for improved planning of radiation therapy procedure comprising
- a) means for acquiring anatomical imaging information,
- b) means for specifying and determining the absolute grade of cell degeneracy by in-vitro tests, whereby marker(s) indicative for specific cell degeneracy are detected and quantified,
- c) means for acquiring functional imaging information,
- d) means for establishing a biology-based segmentation of areas ($k_\alpha$, $k_\beta$, $k_\gamma$) with similar grade of relative cell degeneracy in accordance to information acquired in step a) and c),
- e) means for applying the absolute grade of cell degeneracy according to information acquired in step b) to the biology-based segmentation data, thereby establishing an improved radiation therapy planning procedure.

In one advantageous embodiment of the invention, the system for improved planning of radiation therapy procedure further comprises means for selecting at least one targeted imaging agent specific for the detected indication of cell degeneracy.

In another advantageous embodiment of the invention the system further comprise means for modelling, clustering and/or correcting the information acquired in any of step(s) a) to e).

Said modelling, clustering and/or correction can be realized by software-implemented algorithms or computer programs or empiric correlations, which manage the acquisition, storage, transfer, analysis, grouping, combination, modelling, clustering, correction, optimization, application and/or visualization of the acquired intermediate patient data to and from patient databases.

One possible variation of the present invention displays an automated (computer- and/or robot-controlled) procedure for improved therapy planning.

In another advantageous embodiment of the invention, integration of absolute and relative grade of cell degeneracy is managed by means working according to the equation:

$$D(k; G_{cell\ degeneracy}) = D_0 + \frac{k - k_\alpha}{k_\gamma - k_\alpha} \cdot \Delta D(G_{cell\ degeneracy})$$

where is hypothesized: $\Delta D \propto G_{cell\ deg\ eneracy}$
and wherein
$G_{cell\ deg\ eneracy}$=absolute grade of cell degeneracy,
D=absolute dose of radiation prescribed according to determined biological parameters
$D_0$=dose of radiation according to standard protocol,
$\Delta D$=dose of radiation correlated to absolute cell degeneracy,
$k_\alpha$, $k_\beta$, $k_\gamma$=area with similar grade of relative cell degeneracy.

In yet another advantageous embodiment of the invention the means for functional and/or anatomical imaging comprise means for realizing CT (computed tomography), SPECT (single photon emission computed tomography), PET (positron emission tomography), MRI (magnetic resonance imaging), US (ultrasound), OI (optical imaging), TI (thermal imaging) or X-ray or any combination thereof.

In another advantageous embodiment of the invention, means for anatomical imaging are CT or MRI.

In another advantageous embodiment of the invention, means for multimodality processes like CT/PET, MRI/PET or CT/MRI/PET are used to acquire more exact anatomical imaging information, as for example the more exact determination of tumour boarders within the degenerated tissue or the status of metastasis. A more favourable variation of the invention is anatomical imaging via means for a combined CT/$^{18}$F-FDG-PET procedure.

In one advantageous embodiment of the invention, means for acquiring functional imaging information are PET or SPECT.

In yet another advantageous embodiment of the invention, means for acquiring functional imaging information are $^{18}$F-FMISO-PET.

Advantageous variations of the invention are means for in-vitro tests, e.g. genetic and/or proteomic tests, comprising gene expression profiling, differential display, gel electrophoresis, SAGE, PCR, reverse transcriptase-PCR, quantitative real-time-PCR, protein assays, ELISA or any kind of mass spectrometry-(MS)-based techniques or any combination thereof. Said means might be used with or without (additional) means for cleaning, fractionation, or enrichment of biomaterial or biomarkers.

In another advantageous embodiment of the invention, means for in-vitro test are protein/peptide mass spectrometry (MS), e.g. by MALDI or SELDI or any other MS technique. More favourable are means for MALDI-ToF-MS or SELDI-ToF-MS.

In an alternative advantageous embodiment of the invention, means for in-vitro tests are means for high-through-put screening and analysis, respectively, realized for example on biochips or with the help of biosensor devices.

In one advantageous variation of the present invention, means for in-vitro tests detect CAP43 protein, modifications thereof, metabolic products generated during modification or any combination of proteins and/or metabolic products indicative for hypoxia.

Another advantageous development of the present invention is a system for use in automated procedures of diagnosis and/or therapy management of cancer.

One important advantage of the present invention is the specification of phenotype of cell degeneracy via in-vitro tests.

This allows the specific selection of contrast agents, which are highly specific for the determined medical indication, thereby increasing the quality of functional imaging.

This results in a more accurate determination of absolute grade of degeneracy and spatial distribution.

This in addition makes the procedure for therapy planning more cost- and time-efficient and thus of great importance and advantage for the patient's benefit.

Further, one of the most important advantages of the present invention is the determination of absolute grade of cell degeneracy by in-vitro tests.

This is of enormous importance, because until now dose of radiation or chemotherapeutics administered to the patients is estimated on relatively vague factors like wisdom and experience.

Now, a measured value of degeneracy is used to calibrate or normalize the relative information of functional imaging.

With other words, it is the benefit of the present invention, to apply the absolute grade of cell degeneracy to a map of values of relative degeneracy as a function of spatial distribution of more or less aggressive tumour cell types.

It is the benefit of the present invention that the dose of radiation can be adapted to the individual tumour situation of the patient (e.g. grade, extent, aggressiveness, prognosis of proliferation and metastasis, and recidivism, rescpectivley).

Because radiation therapy is optimized and preferably, the admission of radiation is significantly decreased, a chemotherapy planning procedure might be adapted accordingly and optimized as well, since radiation and chemo therapy are often combined and correlated in complex therapy protocols.

In consequence, the present invention allows an improved therapy planning protocol and corresponding procedure of establishment. The multi-dimensional data acquisition of the present invention realizes an improved and preferably automated procedure of planning a diagnostic and therapeutic approach in terms of rapidity, cost-efficiency, sensitivity, specificity and predictive value in tumour management.

All together, the present invention provides an important opportunity for reducing the burden and increasing the benefit of tumour cancer patients.

The invention has been described with reference to one or more preferred embodiments. Clearly, modifications and alterations will occur upon a reading and understanding of this specification. It is intended to include all such modifications and alterations insofar as they come within the scope of the appended claims or equivalents thereof.

One skilled in the art should realize that the following embodiments are not meant to limit the invention, but merely provide examples incorporating the principles of the invention.

The following example concerns inoperable non-small cell lung cancer:

1. Acquisition of anatomical imaging information using CT of the thorax (standard chest protocol with 90 mAs and 120 kVp): 3D CT data set 2. Quantification of the concentration of the CAP43 protein (42835 Da representing hypoxia protein NDRG1 in humans) in a serum sample: $G_{cell\ degeneracy}$.

Step 1: Sample dilution

To a 96 well plate, add 288 µL of 100 mM Natrium phosphate buffer, pH 7.0

To the plate containing the 100 mM Natrium phosphate buffer, pH 7.0, add 12 µL patient serum sample (1:25 dilution)

Mix and incubate 15 min at room temperature

Step 2: Chip pre-treatment

Add 100 µL 100 mM Natrium phosphate buffer, pH 7.0 to each chip spot (e.g. Ciphergen Q10 chip (strong anion exchange); Ciphergen Biosystems, Inc., USA)

Incubate 5 min

Remove liquid

Repeat pre-treatment once

Step 3: Sample incubation on chips

Add 25 µL of diluted sample to each chip spot

Incubate for 30 minutes at room temperature with shaking

Step 4: Chip wash

Buffer wash chips 3 times: Add 100 µL buffer (100 mM Natrium phosphate buffer, pH 7.0), mix briefly, remove Water wash chips 2 times: Add 150 µL water (Millipore or Milli-Q grade water), mix briefly, remove Air dry chips at least 15 min or until dry Step 5: Matrix addition Add 1 µL of MS matrix solution (50% Acetonitrile/water, 0.5% TFA (Trifluoric acid), SPA (Sinapinic acid) (10 mg/ml)) to each chip spot and let dry 15 min Add 1 µL of MS matrix solution (50% Acetonitrile/water, 0.5% TFA, SPA (10 mg/ml)) to each chip spot and let dry 15 min Place chip into SELDI ToF mass spectrometer Step 6: Analysis; Record MS spectra Identify peak at 42835 Da representing the hypoxia protein NDRG1 in humans Compare peak height and/or peak area with calibration curve representing NDRG 1 concentrations for various levels of hypoxia to determine presence and degree of hypoxia If the absolute grade of cell degeneracy shows that the tumour is non-hypoxic, a standard treatment protocol is taken, e.g. $D_0$=60 Gy (2 Gy/fraction, 5 days per week over 6 weeks; American Society of Clinical Oncology, (1997), Clinical practice guidelines for the treatment of unresectable non-small-cell lung cancer., J Clin Oncol 15: 2996-3018) is used uniformly across the tumour mass.

If the absolute grade of cell degeneracy indicates the presence of hypoxia in the tumour the following steps are executed:

3. Acquisition of a dynamic series of $^{18}$F-FMISO-PET images from the thorax comprising 33 frames acquired over 4 hours using the following acquisition protocol:

31 dynamic frames from 0 to 15 min initiated immediately after tracer injection (12×10 s, 8×15 s, 11×1 min frames) and two late time static scans at 2 h and 4 h post injection.

Average integration times for the late static scans are 5 min for the earlier and 10 min for the later one, individual times vary slightly with patient's weight. A total activity of 350-450 MBq $^{18}$F-FMISO (depending on patient's weight) is intravenously injected within 12 seconds with an automated bolus injection technique (Eschmann S M, Paulsen F, Reimold M, et al., "Prognostic impact of hypoxia imaging with 18F-misonidazole PET in non-small cell lung cancer and head and neck cancer before radiotherapy", J Nucl Med. Feb; 46(2): 253-60, 2005).

4a. Establishing a parametric map of hypoxia according to information acquired in functional imaging, whereby pharmacokinetic analysis of $^{18}$F-FMISO images is executed.

Pharmacokinetic analysis of $^{18}$F-FMISO image sequence is performed by using the Casciari model (J. J. Casciari, M. M. Graham, and J. S. Rasey, "A modeling approach for quantifying tumour hypoxia with [F-18]fluoromisonidazole PET time-activity data", *Med Phys*, 22(7): 1127-39, July 1995).

A parameter, which describes the trapping rate of metabolized $^{18}$F-FMISO, is hypothesized to correlate linearly with oxygen partial pressure (oxygen saturation). This correlation yields a parametric map specifying the oxygen partial pressure of individual pixels corresponding to the resolution of the $^{18}$F-FMISO image. The relevant parameter is $K_A$ (using the nomenclature of Casciari), whereby a value of zero means no hypoxia.

4b. Establishing a biology-based segmentation of areas $k_\alpha$, $k_\beta$ and $k_\gamma$, whereby information of parametric map is applied to a clustering technique. Thus, modulated functional data of the parametric map are combined with data acquired in anatomical imaging (CT). Here, the contour of the tumour is outlined using the CT image data. Through clustering functional data of established parametric map said tumour region is segmented into sub-regions (areas) with low, medium and high hypoxia, represented by the centroids of the clusters, named $k_\alpha$, $k_\ominus$ and $k_\gamma$, respectively.

To cluster the tumour pixels into sub-regions of relative grade of cell degeneracy, a k-mean classifier clustering technique is used.

Clustering is based on co-registration of anatomical location of voxels of target region and organs of risk and functional imaging data (parametric map) into sub-regions (areas) of similar radiation sensitivity. The total number of sub-regions (areas) depends on the noise content and the parameter range of the parametric map. This is because two sub-regions can generally be discriminated in a noisy environment if the difference of the sub-region-representative intensities is at minimum five times greater than the noise. This is based on the model of image detection which states similar criteria for a reliable detection of a uniform object in a noisy background, namely that the ratio of signal difference $\Delta S$ and noise $\sigma_s$ shall be greater than five, or:

$$\frac{\Delta S}{\sigma_S} \geq 5 \qquad (1)$$

Consequently, the number of areas can be determined in accordance with:

$$\# \text{areas} = \frac{k_{MAX} - k_{MIN}}{K \cdot \langle \sigma_k \rangle} \qquad (2)$$

in which, $k_{MAX}$ and $k_{MIN}$ are the maximum and minimum parameter value, respectively, of the target volume; $\langle \sigma_k \rangle$ is the standard deviation representative of the noise in the parametric map; and K is a constant with a value of five or greater according to (1). It should be appreciated that K can be experimentally determined in order to optimize the system.

Said clustering yields in segmentation of tumour region, with a relative scale of tumour hypoxia across the tumour resulting in a dose prescription as follows:

$$D(k; G_{cell\ degeneracy}) = D_0 + \frac{k - k_\alpha}{k_\gamma - k_\alpha} \cdot \Delta D(G_{cell\ degeneracy})$$

where is hypothesized: $\Delta D \propto G_{cell\ deg\ eneracy}$
and wherein
$G_{cell\ deg\ eneracy}$=absolute grade of cell degeneracy,
D=absolute dose of radiation prescribed according to determined biological parameters
$D_0$=dose of radiation according to standard protocol,
$\Delta D$=dose of radiation correlated to absolute cell degeneracy,
k, $k_\alpha$, $k_\gamma$=area with similar grade of relative cell degeneracy.

5. Applying the absolute hypoxia grade (in-vitro test; item 2) to the biology-based segmentation data, thereby correlating that a population of patients with a similar (grade of) disease (according to a patient database) receives a boost dose of $\Delta D$=20 Gy and the cluster centroids are $k_\alpha$=0.005, $k_\beta$=0.020, and $k_\gamma$=0.050, the following dose descriptions for the areas alpha, beta and gamma are recommended:

The weak hypoxia area with $k_\alpha$=0.005 receives the standard dose of $D_\alpha$=60 Gy.

The medium hypoxic area with $k_\beta$=0.020 receives a slightly elevated dose of $$D_\beta = 60\ Gy + \frac{0.020 - 0.005}{0.050 - 0.005} \cdot 20\ Gy = 67\ Gy.$$

And for the strong hypoxic area labeled with gamma the dose to be prescribed is $D_\gamma$=80 Gy.

6. Administering said radiation doses to the determined areas of alpha, beta and gamma of the patient's tumour by the use of standard multi-leave-collimators.

(S. Webb, "Intensity-modulated radiation therapy", Institute of Physics Publishing Ltd 2001).

The invention claimed is:

1. An improved radiation therapy planning procedure comprising the steps of
a) specifying and determining the absolute grade of cell degeneracy by in-vitro tests, whereby marker(s) indicative for specific cell degeneracy are detected and quantified, b) establishing a biology-based segmentation of areas ($k_\alpha$, $k_\beta$, $k_\gamma$) with similar grade of relative cell degeneracy in accordance to information acquired in functional and/or anatomical imaging, c) applying the absolute grade of cell degeneracy to the biology-based segmentation data, thereby establishing an improved radiation therapy planning procedure.

2. An improved radiation therapy planning procedure of claim 1, wherein the integration of absolute and relative grade of cell degeneracy is managed according to the equation:

$$D(k; G_{cell\ degeneracy}) = D_0 + \frac{k - k_\alpha}{k_\gamma - k_\alpha} \cdot \Delta D(G_{cell\ degeneracy})$$

where is hypothesized: $\Delta D \propto G_{cell\ degeneracy}$
and wherein
$G_{cell\ deg\ eneracy}$ = absolute grade of cell degeneracy,
D = absolute dose of radiation prescribed according to determined biological parameters
$D_0$ = dose of radiation according to standard protocol,
$\Delta D$ = dose of radiation correlated to absolute cell degeneracy,
k, $k_\alpha$, $k_\gamma$ = area with similar grade of relative cell degeneracy.

3. An improved radiation therapy planning procedure of claim 1, comprising the step of selecting at least one targeted imaging agent specific for the detected indication of cell degeneracy.

4. An improved radiation therapy planning procedure of claim 1, comprising the provision of procedure(s) of modelling, clustering and/or correcting which can be realized by software-implemented algorithms and/or computer programs and/or empiric correlations which manage the acquisition, storage, transfer, analysis, grouping, combination, modelling, clustering, correction, optimization, application and/or visualization of the acquired intermediate patient data to and from patient databases.

5. An improved radiation therapy planning procedure of claim 1, comprising the provision of procedure(s) for automated (computer- and/or robot-controlled) improved therapy planning.

6. An improved radiation therapy planning procedure of claim 1, comprising the steps of
d) acquiring anatomical imaging information,
e) specifying and determining the absolute grade of cell degeneracy by in-vitro tests, whereby marker(s) indicative for specific cell degeneracy are detected and quantified,
f) acquiring functional imaging information concerning spatial distribution and relative grade of indicated cell degeneracy,
g) establishing a biology-based segmentation of areas ($k_\alpha$, $k_\beta$, $k_\gamma$) with similar grade of relative cell degeneracy in accordance to information acquired in step a) and c),
h) applying the absolute grade of cell degeneracy according to information acquired in step b) to the biology-based segmentation data, thereby establishing an improved radiation therapy planning procedure.

7. An improved radiation therapy planning procedure of claim 6, wherein the anatomical imaging process is CT or MRI.

8. An improved radiation therapy planning procedure of claim 1, wherein the in-vitro tests of step b) are genetic and/or proteomic tests and/or techniques to identify and/or quantify metabolites corresponding to cancer, comprising gene expression profiling, differential display, gel electrophoresis, SAGE, PCR, reverse transcriptase-PCR, quantitative real-time-PCR, protein assays, ELISA or any kind of mass spectrometry-(MS)-based techniques or any combination thereof.

9. An improved radiation therapy planning procedure of claim 1, wherein the in-vitro test is protein/peptide mass spectrometry (MS) by MALDI-ToF or SELDI-ToF.

10. An improved radiation therapy planning procedure of claim 1, wherein the CAP43 protein, modifications thereof, metabolic products generated during modification or any combination of proteins and/or metabolic products indicative for hypoxia is determined in-vitro.

11. An improved radiation therapy planning procedure of claims 1, wherein the functional imaging process is $^{18}$F-FMISO-PET.

12. An improved radiation therapy planning procedure of claim 1, comprising the steps of
i) acquiring anatomical imaging information in CT, i.specifying and determining the absolute grade of cell degeneracy by in-vitro tests, whereby CAP 43 protein, modifications thereof, metabolic products generated during modification or any combination of proteins and/or metabolic products indicative for hypoxia is detected and quantified,
j) selecting $^{18}$F-FMISO as targeted imaging agent,
k) acquiring functional imaging information concerning spatial distribution and relative grade of indicated cell degeneracy in $^{18}$F-FMISO-PET,
l) establishing a biology-based segmentation of areas ($k_\alpha$, $k_\beta$, $k_\gamma$) with similar grade of relative cell degeneracy in accordance to information acquired in step a) and d),
m) applying the absolute grade of cell degeneracy according to information acquired in step b) to the biology-based segmentation data, thereby establishing an improved radiation therapy planning procedure.

13. System for improved planning of radiation therapy procedure comprising
n) means for specifying and determining the absolute grade of cell degeneracy in in-vitro tests, whereby marker(s) indicative for specific cell degeneracy are detected and quantified,
o) means for establishing a biology-based segmentation of areas ($k_\alpha$, $k_\beta$, $k_\gamma$) with similar grade of relative cell degeneracy in accordance to information acquired in functional and/or anatomical imaging,
p) means for applying the absolute grade of cell degeneracy to the biology-based segmentation data, thereby establishing an improved radiation therapy planning procedure.

14. System for improved planning of radiation therapy procedure of claim 13, wherein the integration of absolute and relative grade of cell degeneracy is managed by means working according to the equation:

$$D(k; G_{cell\ degeneracy}) = D_0 + \frac{k - k_\alpha}{k_\gamma - k_\alpha} \cdot \Delta D(G_{cell\ degeneracy})$$

where is hypothesized: $\Delta D \propto G_{cell\ deg\ eneracy}$
and wherein
$G_{cell\ deg\ eneracy}$ = absolute grade of cell degeneracy,
D = absolute dose of radiation prescribed according to determined biological parameters
$D_0$ = dose of radiation according to standard protocol,
$\Delta D$ = dose of radiation correlated to absolute cell degeneracy, k, $k_\alpha$, $k_\gamma$=area with similar grade of relative cell degeneracy.

15. System for improved planning of radiation therapy procedure of claim 13, further comprising means for selecting at least one targeted imaging agent specific for the detected indication of cell degeneracy.

16. System for improved planning of radiation therapy procedure of claim 13, comprising means for modelling, clustering and/or correcting which can be realized by software-implemented algorithms and/or computer programs and/or empiric correlations which manage the acquisition, storage, transfer, analysis, grouping, combination, modelling, clustering, correction, optimization, application and/or visualization of the acquired intermediate patient data to and from patient databases.

17. System for improved planning of radiation therapy procedure of claim 13, comprising means for automated (computer-and/or robot-controlled) therapy planning.

18. System for improved planning of radiation therapy procedure of claim 13, comprising
   q) means for acquiring anatomical imaging information,
   r) means for specifying and determining the absolute grade of cell degeneracy in in-vitro tests, whereby marker(s) indicative for specific cell degeneracy are detected and quantified,
   s) means for acquiring functional imaging information,
   t) means for establishing a biology-based segmentation of areas ($k_\alpha$, $k_\beta$, $k_\gamma$) with similar grade of relative cell degeneracy in accordance to information acquired in step a) and c),
   u) means for applying the absolute grade of cell degeneracy according to information acquired in step b) to the biology-based segmentation data, thereby establishing an improved radiation therapy planning procedure.

19. System for improved planning of radiation therapy procedure of claim 18, wherein means for anatomical imaging is CT or MRI.

20. System for improved planning of radiation therapy procedure claim 13, wherein means for in-vitro tests are genetic and/ or proteomic techniques and/or techniques for identification and/or quantification of metabolites corresponding to cancer, comprising gene expression profiling, differential display, gel electrophoresis, SAGE, PCR, reverse transcriptase-PCR, quantitative real-time-PCR, protein assays, ELISA or any kind of mass spectrometry-(MS)-based techniques or any combination thereof.

21. System for improved planning of radiation therapy procedure of claim 13, wherein means for in-vitro test is protein/peptide mass spectrometry (MS) by MALDI-ToF or SELDI-ToF.

22. System for improved planning of radiation therapy procedure of claim 13, wherein means for in-vitro tests detecting CAP43 protein, modifications thereof, metabolic products generated during modification or any combination of proteins and/or metabolic products indicative for hypoxia.

23. System for improved planning of radiation therapy procedure of claim 13, wherein means for acquiring functional imaging information is $^{18}$F-FMISO-PET.

24. System according to claim 13 for use in procedures of diagnosis and/or therapy management of cancer.

\* \* \* \* \*